US012697123B2

(12) United States Patent
Shuman et al.

(10) Patent No.: US 12,697,123 B2
(45) Date of Patent: Aug. 4, 2026

(54) AIRWAY VALVE APPARATUS

(71) Applicant: GYRUS ACMI, INC., Westborough, MA (US)

(72) Inventors: Brandon Shuman, Kirkland, WA (US); Clint Finger, Bellevue, WA (US); Lisa Lauer, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 1020 days.

(21) Appl. No.: 16/493,040

(22) PCT Filed: Mar. 23, 2017

(86) PCT No.: PCT/US2017/023701
§ 371 (c)(1),
(2) Date: Sep. 11, 2019

(87) PCT Pub. No.: WO2018/174878
PCT Pub. Date: Sep. 27, 2018

(65) Prior Publication Data
US 2020/0113574 A1      Apr. 16, 2020

(51) Int. Cl.
*A61B 17/12* (2006.01)
*A61B 17/00* (2006.01)
*A61F 2/04* (2013.01)

(52) U.S. Cl.
CPC .. *A61B 17/12104* (2013.01); *A61B 17/12036* (2013.01); *A61B 17/1204* (2013.01);
(Continued)

(58) Field of Classification Search
CPC ........ A61B 17/12104; A61B 17/12036; A61B 17/1204; A61B 17/12172; A61F 2/04;
(Continued)

(56) References Cited

U.S. PATENT DOCUMENTS

| | | | |
|---|---|---|---|
| 5,855,601 A | 1/1999 | Bessler | |
| 6,929,637 B2 | 8/2005 | Gonzalez | |

(Continued)

FOREIGN PATENT DOCUMENTS

| | | |
|---|---|---|
| CN | 1810316 A | 8/2006 |
| CN | 102112073 A | 6/2011 |

(Continued)

OTHER PUBLICATIONS

International Search Report, PCT/2017/023701, dated Dec. 12, 2017.
(Continued)

*Primary Examiner* — Darwin P Erezo
*Assistant Examiner* — Raihan R Khandker
(74) *Attorney, Agent, or Firm* — Schwegman Lundberg & Woessner, P.A.

(57) ABSTRACT

An airway valve apparatus 10 for at least partially sealing an airway 30 of a subject 40 comprising: a hub 50; a plurality of anchor struts 60 disposed about and in communication with the hub; a plurality of support struts 70 disposed about and in communication with the hub; one or more membranes that are in communication with the plurality of anchor struts, the plurality of support struts, or both; and wherein the anchor struts include one or more anchor elements 62 disposed at a distal end of the anchor struts, the one or more anchor elements configured to engage a wall 32 of the airway.

19 Claims, 4 Drawing Sheets

(52) U.S. Cl.
 CPC .......... *A61B 17/12172* (2013.01); *A61F 2/04* (2013.01); *A61B 2017/0034* (2013.01); *A61B 2017/1205* (2013.01); *A61B 17/12177* (2013.01); *A61F 2002/043* (2013.01); *A61F 2220/0016* (2013.01); *A61F 2230/0093* (2013.01); *A61F 2250/0018* (2013.01); *A61F 2250/0036* (2013.01); *A61F 2250/0059* (2013.01)

(58) Field of Classification Search
 CPC ........ A61F 2002/043; A61F 2220/0016; A61F 2230/0093; A61F 2250/0018; A61F 2250/0036; A61F 2250/0059; A61F 2002/016
 See application file for complete search history.

(56) References Cited

U.S. PATENT DOCUMENTS

| | | | |
|---|---|---|---|
| 6,941,950 | B2 | 9/2005 | Wilson et al. |
| 7,011,094 | B2 | 3/2006 | Rapacki |
| 7,451,765 | B2 | 11/2008 | Adler |
| 7,670,373 | B1 | 3/2010 | Sabanathan |
| 7,691,151 | B2 | 4/2010 | Kutsko |
| 7,854,228 | B2 | 12/2010 | Wilson et al. |
| 7,875,048 | B2 | 1/2011 | Dillard et al. |
| 7,887,585 | B2 | 2/2011 | Gonzalez |
| 8,257,381 | B2 | 9/2012 | Dillard |
| 8,338,682 | B1 | 12/2012 | Sikra |
| 8,414,655 | B2 | 4/2013 | Alferness |
| 8,444,690 | B2 | 5/2013 | Gonzalez |
| 8,454,708 | B2 | 6/2013 | Kutsko |
| 8,603,127 | B2 | 12/2013 | Alferness |
| 8,647,392 | B2 | 2/2014 | Kutsko |
| 8,956,319 | B2 | 2/2015 | Dillard et al. |
| 8,974,527 | B2 | 3/2015 | Gonzalez |
| 9,622,752 | B2 | 4/2017 | Gonzalez |
| 2003/0050648 | A1 | 3/2003 | Alferness |
| 2003/0050682 | A1 | 3/2003 | Sharkey |
| 2003/0127090 | A1 | 7/2003 | Gifford |
| 2003/0154988 | A1 | 8/2003 | DeVore et al. |
| 2003/0158515 | A1 | 8/2003 | Gonzalez et al. |
| 2003/0181922 | A1 | 9/2003 | Spiration |
| 2004/0143282 | A1 | 7/2004 | Dillard |
| 2005/0033344 | A1 | 2/2005 | Dillard |
| 2005/0137714 | A1 | 6/2005 | Gonzalez |
| 2006/0102186 | A1 | 5/2006 | Adler |
| 2007/0232992 | A1 | 10/2007 | Kutsko et al. |
| 2014/0031849 | A1 | 1/2014 | Gonzalez |
| 2014/0371778 | A1 | 12/2014 | Rudakov et al. |
| 2016/0015394 | A1* | 1/2016 | Cedro, Jr. ........ A61B 17/12131 606/139 |
| 2016/0030221 | A1 | 2/2016 | Wan |
| 2017/0035562 | A1 | 2/2017 | Quadri |
| 2017/0172722 | A1* | 6/2017 | Dillard .................. A61B 1/012 |
| 2017/0181665 | A1 | 6/2017 | Johnson |
| 2017/0281330 | A1 | 10/2017 | Liljegren |
| 2019/0029691 | A1* | 1/2019 | Liljegren ......... A61B 17/12036 |
| 2019/0059906 | A1* | 2/2019 | Liljegren ......... A61B 17/12172 |
| 2021/0093434 | A1* | 4/2021 | Chen .................... A61F 2/0108 |

FOREIGN PATENT DOCUMENTS

| | | | |
|---|---|---|---|
| CN | 102580171 | A | 7/2012 |
| CN | 106413588 | A | 2/2017 |
| CN | 110636802 | A | 12/2019 |
| CN | 110636802 | B | 10/2022 |
| DE | 112017007300 | T5 | 1/2020 |
| GB | 2574754 | A | 12/2019 |
| GB | 2574754 | B | 12/2021 |
| JP | 2005520631 | A | 7/2005 |
| JP | 2020509902 | A | 4/2020 |
| WO | 2002/094087 | A1 | 11/2002 |
| WO | 2003/079944 | A1 | 10/2003 |
| WO | 2004/010845 | A2 | 2/2004 |
| WO | 2004/103209 | A2 | 12/2004 |
| WO | 2005102211 | A1 | 11/2005 |
| WO | 2013/040431 | A1 | 3/2013 |
| WO | 2015/153507 | A1 | 10/2015 |
| WO | WO-2017172021 | A1 | 10/2017 |
| WO | WO-2018174878 | A1 | 9/2018 |

OTHER PUBLICATIONS

"Chinese Application Serial No. 201780088576.X, Office Action mailed Mar. 2, 2022", w/ English translation, 16 pgs.

"Chinese Application Serial No. 201780088576.X, Response filed Jul. 4, 2022 to Office Action mailed Mar. 2, 2022", w/ English claims, 7 pgs.

"International Application Serial No. PCT/US2017/023701, International Preliminary Report on Patentability mailed Oct. 3, 2019", 7 pgs.

"International Application Serial No. PCT/US2017/023701, Written Opinion mailed Dec. 20, 2017", 5 pgs.

"Japanese Application Serial No. 2019-552278, Office Action mailed Oct. 6, 2020", with machine translation, 8 pgs.

"Japanese Application Serial No. 2019-552278, Written Amendment filed Mar. 15, 2021", with English translation of claims, 4 pgs.

"United Kingdom Application Serial No. 1913415.4, Examination Report mailed Jul. 16, 2021", 4 pgs.

"United Kingdom Application Serial No. 1913415.4, Intention to Grant under Section 18(4) mailed Sep. 27, 2021", 2 pgs.

"United Kingdom Application Serial No. 1913415.4, Response filed Sep. 16, 2021 to Office Action mailed Jul. 16, 2021", 6 pgs.

* cited by examiner

AIRWAY VALVE APPARATUS

FIELD

The present teachings generally relate to an improved removable airway valve apparatus for at least partially blocking a passageway of a subject's lung.

BACKGROUND

The present teachings are predicated upon providing an improved removable airway valve apparatus that allows a user to at least partially block a passageway (airway) of a subject's lung. Currently, there are a number of devices that are on the market that are directed at this function, for example: SVS valve by Spiration and the Zephyr valve by Pulmonx. Patents and publications related to these known devices and/or methods include: U.S. Pat. Nos. 8,956,319; 8,603,127; 8,414,655; 8,338,682; 7,875,048; 6,941,950; and WO 2004/010845, the teachings of which are expressly incorporated by reference herein in their entirety for all purposes.

Some of the valve devices may be conformable to the size of the airway such that the airway does not need to be measured and a one size fits all device may be employed. However, if the size of the device is not selected properly or the device is not set in the airway, the device may be expelled (e.g., coughed out) or may move within the passageway such that the effectiveness of the device is reduced. An example of such a device is found in U.S. Pat. No. 7,854,228 the teachings of which are expressly incorporated by reference herein in their entirety for all purposes.

Some of the valve devices may be less conformable to the size of the airway such that the airway does need to be measured and a selectable sized device may be employed. However, even if the size of the device is selected properly or the device is not set in the airway, the device may be expelled (e.g., coughed out) or may move within the passageway such that the effectiveness of the device is reduced.

Some of the valve devices allow somewhat for the natural flow of mucus (via Tiny broom-like structures (cilia)) from the section of the lung that is being blocked by the valve device. Some of the other devices, by the nature of their structure, do not allow for the natural flow of mucus.

It would be attractive to have a valve device that functions properly over a wide range of airway sizes and shapes (e.g. non-round passageways), and allows for high-pressure events (e.g. coughing) without being expelled. What is needed is an airway valve apparatus that has structural features that balance the above stated needs.

SUMMARY

The present teachings/invention meet one or more (if not all) of the present needs by providing an apparatus comprising: An airway valve apparatus 10 for at least partially sealing an airway 30 of a subject 40 comprising: a hub 50; a plurality of anchor struts 60 disposed about and in communication with the hub; a plurality of support struts 70 disposed about and in communication with the hub; one or more membranes that are in communication with the plurality of anchor struts, the plurality of support struts, or both; and wherein the anchor struts include one or more anchor elements 62 disposed at a distal end of the anchor struts, the one or more anchor elements configured to engage a wall 32 of the airway.

The present teachings/invention also may include a combination of one or more of the following: a first anchor portion 64 of the plurality of anchor struts has at least first stiffness value, a first support portion 76 of the plurality of support struts has at least second stiffness value, and wherein the first stiffness value is greater than the second stiffness value; the first stiffness value is twenty percent higher than the second stiffness value; the first support portion, a second support portion 78 of the plurality of support struts, or both are configured to partially and temporarily collapse towards the rod assembly when subjected to and during a high-pressure event on the one or more membranes; the plurality of support struts is configured to collapse towards a rod assembly 90 and the one or more anchor elements be disengaged the wall of the airway by engaging and pulling on a proximal end 92 of the rod assembly; there are three or more anchor struts and there are two or more support struts disposed in-between each of the three or more anchor struts; the plurality of support struts has a base width 72 and an end width 74, and wherein the base width is greater than the end width; a first anchor portion 64 of the plurality of anchor struts has at least first stiffness value, a first support portion 76 of the plurality of support struts has at least second stiffness value, and wherein the first stiffness value is greater than the second stiffness value; and wherein the support strut having a base width 72 in the first support portion and an end width 74 in a second support portion 78, the base width being larger than the end width and the first support portion exerting a greater radial force than the second support portion; a first anchor portion 64 of the plurality of anchor struts has at least first stiffness value, a first support portion 76 of the plurality of support struts has at least second stiffness value, and wherein the first stiffness value is greater than the second stiffness value; and the anchor strut in the first anchor portion 64 exerts a greater radial force than in a second anchor portion 66.

The present teachings provide a valve device with an inventive structure that is described herein and in the drawing figures.

DETAILED DESCRIPTION

Figure 1:
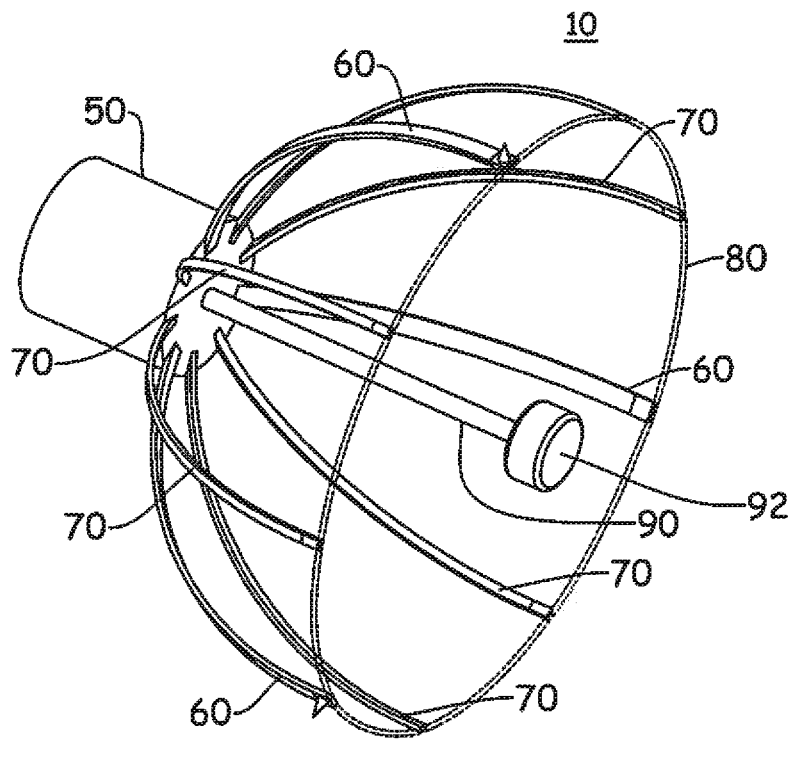
FIG. 1 illustrates a perspective view of one embodiment of the present invention.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are directed to an improved airway valve apparatus. The improved airway valve apparatus functions to block airflow into a portion of a lung by blocking, or at least partially blocking, an air passage (airway) to that portion of the lung. It is contemplated that it can allow for the passage of mucus out of the blocked portion of the lung. It is also contemplated that it will remain in place during and after a high-pressure event (e.g. cough or similar incidence). Furthermore, the apparatus is configured to be removable. The present invention employs a unique anchoring and strut configuration to accomplish the desired performance. Disclosed herein is additional details of the improved apparatus including illustrative examples and preferred embodiments.

Airway Valve Apparatus 10

It is contemplated that the present invention is an airway valve apparatus 10 that is removable and is used to block airflow into a portion of a lung by blocking, or at least partially blocking, an air passage (airway) to that portion of the lung. It is generally installed in to an airway in a collapsed arrangement and expands when deployed. The airway valve apparatus 10 may be comprised of a number of components that form an assembly. Included may be at least a hub 50, a plurality of anchor struts 60, a plurality of support struts 70, and one or more membranes 80. Preferably, the hub 50 operationally connects at least the struts 60, 70 and potentially the one or more membranes 80. Functionally, there may include a structure or feature that may aid in the placement or retrieval of the valve apparatus 10. It is contemplated that this may be a separate structure, for example a rod assembly 90 attached to the hub 50, or may be an area of the struts 60, 70 that can be utilized for this function.

It is also contemplated that the struts 60, 70 may have different stiffness values. These stiffness values may vary along their respective length (e.g. as the struts move away from the hub 50, a first stiffness value, a second stiffness value, etc.) and may also vary between anchor struts 60 and support struts 70. It is generally believed that it is desirable for a stiffness value of the anchor strut 60 to be greater than that of the support strut 70. It is contemplated that the difference in the stiffness values between at least the distal portions thereof (e.g. further away from the hub 50) of the support struts 70 versus the anchor struts 60 are preferably at least about 20 percent less, more preferably at least about 40 percent less, and most preferably about at least 75 percent less. For example, the anchor strut may have a stiffness value of about 0.259 lbf (10.9 millinewton meter) and the membrane support strut may have a stiffness value of about 0.184 lbf (7.75 millinewton meter), both plus or minus the percentages above.

It is also contemplated that the struts 60,70 may be further described as exhibiting a radial force value when deployed in an airway 30. This radial force acts against the airway wall 32, pushing the struts 60, 70 away from the central axis of the apparatus 10.

The apparatus 10 envisioned may, when deployed in the airway 30, may generally have a semi-circular shape (e.g. struts 60,70 and membrane 80) or may have a flatter arcuate shape (similar to that of the SVS valve by Spiration). In a preferred embodiment, the apparatus will have a semi-circular shape in the deployed position.

Airway 30/Subject 40

It is contemplated that the valve apparatus 10 is intended to be used in an airway 30 of a subject 40 (e.g. human patient) to at least partially close off or restrict airflow to and from a portion of a lung. When deployed, or implanted in the lung, one or more anchor elements 62 may engage the wall 32 of the airway 30 to hold the apparatus 10 in place.

Hub 50

It is contemplated that the apparatus 10 may include a hub 50 that functions as a base structure at or near it's center. The hub 50 may provide for a connection point for one or more of the struts 60, 70, a placement or retrieval structure, and/or a membrane 80. In the case of a placement or retrieval structure, it is contemplated that a number of differing structures may be provided. In one example, a hook like structure may be provided on the hub to allow for some forceps to grip when the apparatus 10 is to be removed. In another example, a rod assembly 90 may be provided to serve the same function. The hub 50 may be constructed of any number of bio-compatible materials, such as stainless steel, nitinol, polymeric materials, or any combination thereof. In a preferred embodiment, the hub is constructed of the same material as the struts 50 or 60.

Anchor Struts 60

It is contemplated that the apparatus 10 may include one or more anchor struts 60. These struts 60 function, when deployed and in conjunction with the anchor elements 62, to substantially hold the apparatus in situ in the airway 30 of the subject 40. The struts 60 may be constructed of any number of bio-compatible materials, such as stainless steel, nitinol, polymeric materials, or any combination thereof. In a preferred embodiment, the struts 60 are constructed of nitinol.

It is contemplated that the struts 60 may have one or more geometric configurations. It may include a number of anchor portions that have differing geometric configurations and differing stiffness values. These geometric configurations may be defined as a first anchor portion 64, second anchor portion 66, third anchor portion 68, and so on. Each configuration may provide differing stiffness values, for example, a first stiffness value, a second stiffness value, and so on. Functionally, the stiffness value should be high enough to allow the apparatus 10 to remain in place, in the airway 30, during the treatment duration and not to come loose due to a high-pressure event. Additionally, the stiffness should be sufficiently low enough to allow for the apparatus to be removed after treatment. It is contemplated that these stiffness values may range from about 0.1 to about 0.3 lbf, (4.2 to 12.6 millinewton meter) to more preferably from about 0.1 to 0.4 lbf (4.2 to 16.9 millinewton meter), and most preferably from about 0.05 to about 0.5 lbf (2.1 to 21.1 millinewton meter).

It is contemplated that the geometric configurations in the anchor portions can take many shapes and sizes, so long that it provides the desired stiffness values and functionality. In some illustrative example, in may be desirous to vary the strut thickness from about 0.10 mm at the hub 50 to about 0.025 mm thickness at the distal tip, using a linear relationship over the length of the strut. The length of a strut can be as long as about 6.5 mm to about 7.0 mm and as short as about 3.5 mm to about 4.5 mm depending on the valve 10 size (e.g. 9 mm and 5 mm diameters respectively). It is also contemplated that the strut 60 may vary in strut width from about 0.10 mm at the hub 50 (base width 68) to about 0.025 mm near the distal end (end width 69). Additionally, the strut 60 may vary both width and thickness. In another alternative, and in place of a straight strut, the strut may follow a zig zag pattern. At the hub 50 its straight and thus stiffer, but at the end it zig-zags back and forth to reduce stiffness preferentially as it gets closer to the end.

It is contemplated that the change in width of the beam is directly proportional to the change in stiffness. Therefore, a linear relationship in change of width results in a linear relationship in change in stiffness over the length. The cube of the thickness of the strut is related to the stiffness, so as the thickness increases the stiffness increases by the cube of the thickness. Additionally, it may not be necessary to have a linear relationship between stiffness and compression distance. Therefore, it is not necessary to have a linear relationship between stiffness and length of strut. The relationship between stiffness and length of strut can be linear, or exponential or logarithmic. To achieve these different relationships the thickness and width can be varied accordingly following a standard beam bending formula for Cantilever Beam—Concentrated load P at the free end.

In a preferred embodiment, the strut 60 includes at least two portions, a first anchor portion 64, second anchor portion 66. The first anchor portion is proximal to the hub 50 and the second anchor portion is nearer the distal end of the strut. The first anchor portion 64 may encompass about ¼ to about ¾ of the length or the strut, about ¼ to about % of the length of the strut, and about ¼ to about ⅓ of the length of the strut. The second anchor portion 66 may encompass about ¼ to about ¾ of the length or the strut, about ¼ to about ¾ of the length of the strut, and about ¼ to about ⅓ of the length of the strut.

Anchor Elements 62

It is contemplated that the apparatus 10 includes one or more anchor elements 62. The elements 62 function as the main holding interface between the apparatus 10 and the airway wall 32 and are generally projections at or near the distal end of the anchor struts 60. It is contemplated that they may be integral to the strut 60 (e.g. a turned end portion of the strut 60) or may a separate piece that is attached to the strut 60.

The elements 62 may have a number of geometric configurations and sizes, so long as it is a shape and dimension conducive to holding the apparatus 10 in place, while still allowing for removal of the apparatus 10 without undue trauma to the wall 32. It is contemplated that the anchor struts 60 provide a compressive force (e.g. push outwardly) between the elements 62 and the wall 32, which also helps the apparatus 10 in place. In one preferred embodiment, the element 62 is configured with an arrow shape, with a pointed end directed into the wall 32 when deployed in the airway 30. In another preferred embodiment, the elements 62 are configured as flat tabs that are turned-up extensions of the anchor struts 60.

Support Struts 70

It is contemplated It is contemplated that the apparatus 10 may include one or more support struts 70. These struts 70 function, when deployed and in conjunction with the anchor struts 60, to substantially hold the membrane 80 of the apparatus 10 in situ in the airway 30 of the subject 40. The struts 70 may be constructed of any number of bio-compatible materials, such as stainless steel, nitinol, polymeric materials, or any combination thereof. In a preferred embodiment, the struts 70 are constructed of nitinol.

It is contemplated that the struts 70 may have one or more geometric configurations. It may include a number of anchor portions that have differing geometric configurations and differing stiffness values. These geometric configurations may be defined as a first support portion 76, second support portion 78, third support portion, and so on. Each configuration may provide differing stiffness values, for example, a first stiffness value, a second stiffness value, and so on. Functionally, the stiffness value should be high enough to allow the membrane 80 to remain in place against the airway 30, during the treatment duration but to allow temporary flexing inwards (e.g. towards a central axis of the apparatus 10) due to a high-pressure event. Additionally, the stiffness should be sufficiently low enough to allow for the apparatus to be removed after treatment. It is contemplated that these stiffness values may range from about same range as anchors above.

It is contemplated that the geometric configurations in the anchor portions can take many shapes and sizes, so long that it provides the desired stiffness values and functionality. In some illustrative example, in may be desirous to vary the strut thickness from about 0.10 mm at the hub 50 to about 0.015 mm thickness at the distal tip, using a linear relationship over the length of the strut. The length of a strut can be as long as about 6.5 mm to about 7.0 mm and as short as about 3.5 mm to about 4.5 mm depending on the valve 10 size (e.g. 9 mm and 5 mm diameters respectively). It is also contemplated that the strut 70 may vary in strut width from about 0.10 mm at the hub 50 (base width 72) to about 0.015 mm near the distal end (end width 74). Additionally, the strut 70 may vary both width and thickness. In another alternative, and in place of a straight strut, the strut may follow a zig zag pattern. At the hub 50 its straight and thus stiffer, but at the end it zig-zags back and forth to reduce stiffness preferentially as it gets closer to the end.

It is contemplated that the change in width of the beam is directly proportional to the change in stiffness. Therefore, a linear relationship in change of width results in a linear relationship in change in stiffness over the length. The cube of the thickness of the strut is related to the stiffness, so as the thickness increases the stiffness increases by the cube of the thickness. Additionally, it may not be necessary to have a linear relationship between stiffness and compression distance. Therefore, it is not necessary to have a linear relationship between stiffness and length of strut. The relationship between stiffness and length of strut can be linear, or exponential or logarithmic. To achieve these different relationships the thickness and width can be varied accordingly following a standard beam bending formula for Cantilever Beam—Concentrated load P at the free end.

In a preferred embodiment, the strut 70 includes at least two portions, a first support portion 76, second support portion 78. The first support portion is proximal to the hub 50 and the second support portion is nearer the distal end of the strut 70. The first support portion 76 may encompass about ¼ to about ¾ of the length or the strut, about ¼ to about ½ of the length of the strut, and about ¼ to about ⅓ of the length of the strut. The second support portion 78 may encompass about ¼ to about ¾ of the length or the strut, about ¼ to about ½ of the length of the strut, and about ¼ to about ⅓ of the length of the strut.

Membrane 80

It is contemplated that the apparatus 10 includes a membrane 80 that functions to block the airflow. The membrane 80 may be disposed about and connected to the anchor struts 60, support struts 70, and potentially the hub 50 in a configuration much akin to an umbrella. It is contemplated that the membrane 80 may be a unitary piece of polymeric material, such as polycarbonate-polyurethane, silicone, or an assembly of one or more of these materials. It is desirous that the membrane 80 be flexible and compliant, so that it may form a seal on the wall 32 of the airway 30 when deployed.

Rod Assembly 90

It is contemplated that the apparatus may include a rod assembly 90 that is attached to the hub 50. This rod assembly 90 may function as a placement and removal aid for the apparatus 10. In a preferred embodiment, the rod assembly 90 may include a proximal end head 92 that provides for a grasping surface for a removal device, such as forceps or the like.

Illustrative Examples

Figure 2:
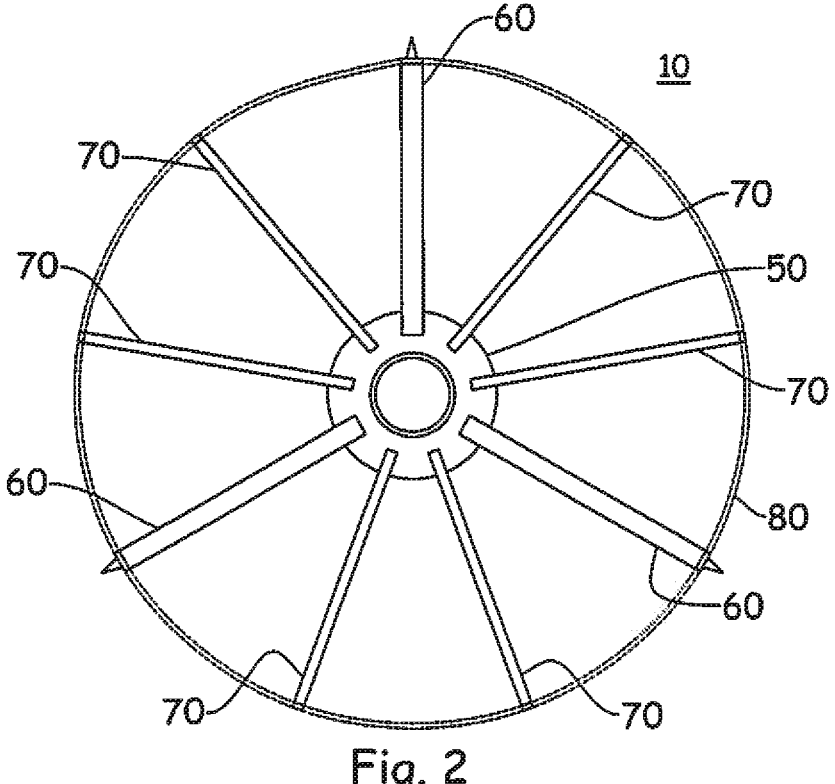
FIG. 2 illustrates a front view of FIG. 1.

FIGS. 1 and 2 illustrates an exemplary apparatus 10, including the hub 50, a plurality of anchor struts 60, a plurality of support struts 70, a membrane 80, and the optional rod assembly 90.

Figure 3:
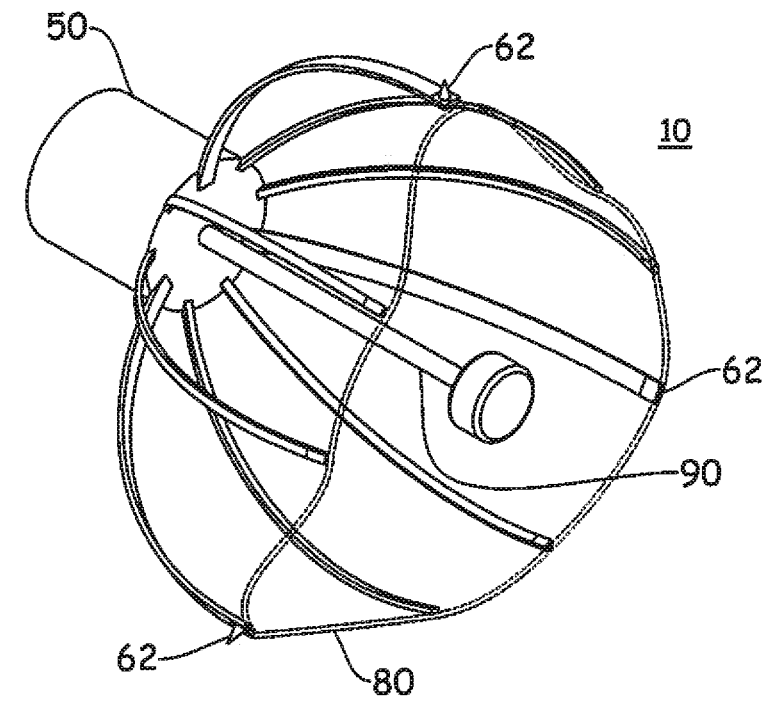
FIG. 3 illustrates a perspective view of one embodiment of the present invention during a high-pressure event.
Figure 4:
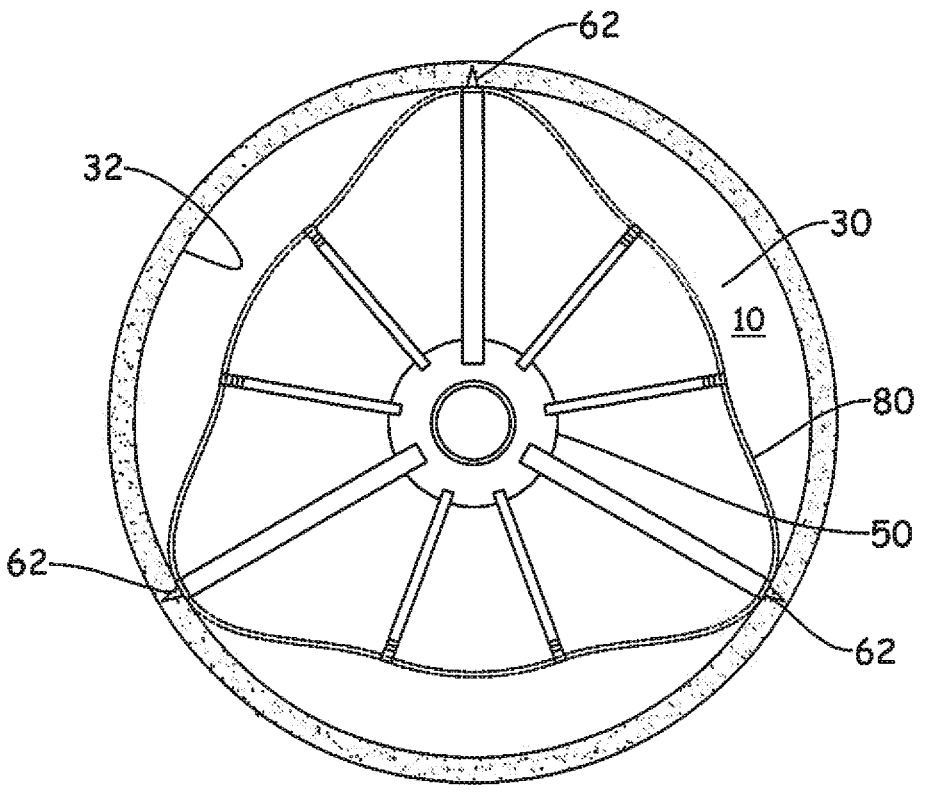
FIG. 4 illustrates a front view of one embodiment of the present invention during a high-pressure event in-situ in an airway.

FIGS. 3 and 4 illustrates an exemplary apparatus 10, during a high-pressure event. The support struts deflect towards the central axis of the apparatus 10 during the event, while the anchors remain intact with the airway wall 32 to keep the apparatus in-place. Arrow style anchor elements 62 are also illustrated.

Figures 5, 6:
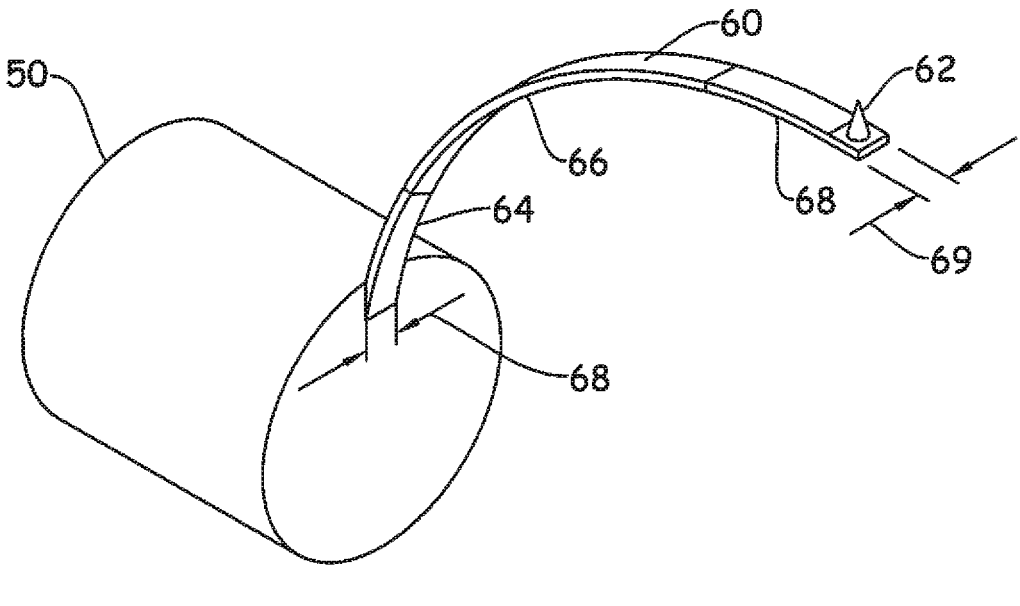
FIG. 5 illustrates a perspective view of the hub and one anchor strut.
FIG. 6. illustrates a perspective view of the hub and one support strut.
Figures 7A, 7B:
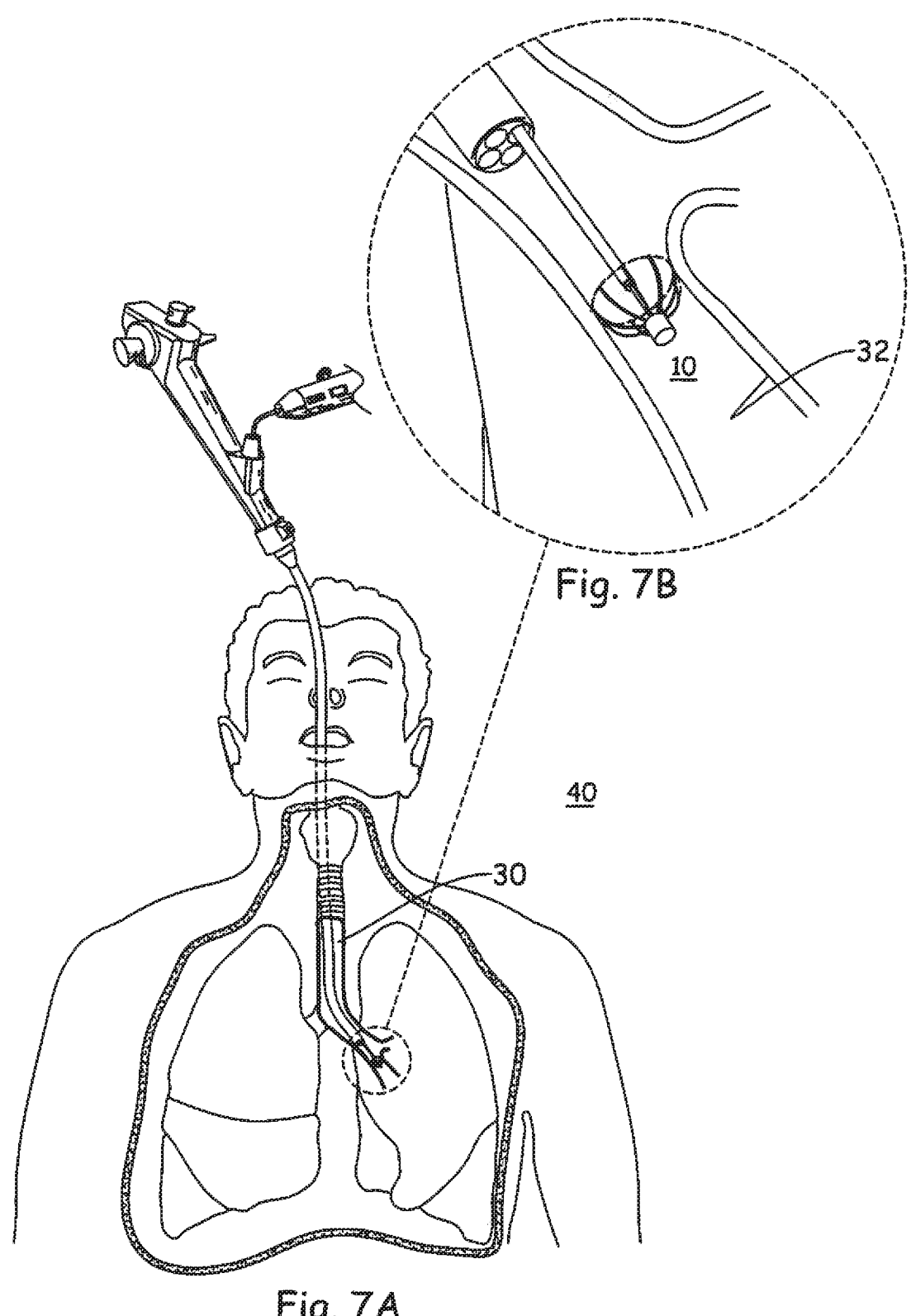
FIG. 7A illustrates a perspective view of the apparatus being deployed in the airway of a subject.
FIG. 7B. illustrates a close up perspective view of the apparatus being deployed in the airway of a subject.

FIGS. 5 and 6 illustrate the sections/portions (64, 66, 68; 76, 78) of the struts 60, 70. Also, showing the base (68, 72) and end (69, 74) widths.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values, which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

ELEMENT LIST airway valve apparatus 10
airway 30
wall 32
subject 40
hub 50
anchor struts 60
anchor elements 62
distal end 64 of the anchor struts
first anchor portion 64
second anchor portion 66
base width 68
end width 69
support struts 70
base width 72
end width 74
first support portion 76
second support portion 78
membranes 80
rod assembly 90
proximal end head 92
We claim:

1. An airway valve apparatus for at least partially sealing an airway of a subject comprising:

a hub;

a plurality of anchor struts disposed about a periphery of the hub and extending from a proximal anchor end that is directly affixed to the hub to a distal anchor end that is distal from the hub, each anchor strut of the plurality of anchor struts including a first stiffness;

a plurality of support struts disposed about the periphery of the hub and extending from a proximal support end that is directly affixed to the hub to a distal support end that is distal from the hub, each support strut of the plurality of support struts including a second stiffness value, wherein the second stiffness value is less than the first stiffness value;

one or more membranes extending distally away from the hub and covering the plurality of anchor struts and the plurality of support struts; and wherein individual distal anchor ends of the plurality of anchor struts include a free terminal end covered by the one or more membranes and each free terminal end includes one or more anchor elements extending through the one or more membranes, the one or more anchor elements configured to engage a wall of the airway.

2. The airway valve apparatus of claim 1, wherein the plurality of anchor struts and the plurality of support struts maintain the one or more membranes with a convex surface facing outward toward the airway.

3. The airway valve apparatus of claim 1:
wherein the first stiffness value is twenty percent higher than the second stiffness value.

4. The airway valve apparatus of according to claim 1:
wherein the plurality of support struts are configured to partially and temporarily collapse towards a rod assembly when subjected to and during a high-pressure event on the one or more membranes.

5. The airway valve apparatus according to claim 1:
wherein the plurality of support struts is configured to collapse towards a rod assembly and the one or more anchor elements are configured to disengage the wall of the airway by engaging and pulling on a proximal end of the rod assembly.

6. The airway valve apparatus according to claim 1, wherein the airway valve apparatus comprises the plurality of anchor struts including three or more anchor struts and the plurality of support struts including two or more support struts disposed in-between each of the three or more anchor struts.

7. The airway valve apparatus according to claim 1:
wherein the plurality of support struts have a base width and an end width, and the base width is greater than the end width.

8. The airway valve apparatus of claim 1,
wherein a first anchor portion of the plurality of anchor struts has at least the first stiffness value, a first support portion of the plurality of support struts has at least the second stiffness value, and the first stiffness value is greater than the second stiffness value; and
wherein each support strut of the plurality of support struts has a base width in the first support portion and an end width in a second support portion, the base width being larger than the end width, and the first support portion exerting a greater radial force than the second support portion.

9. The airway valve apparatus of claim 1,
wherein a first anchor portion of the plurality of anchor struts has at least the first stiffness value, a first support portion of the plurality of support struts has at least the second stiffness value, and the first stiffness value is greater than the second stiffness value; and
wherein the first anchor portion exerts a greater radial force than in a second anchor portion of the plurality of anchor struts.

10. An airway valve apparatus comprising:
a hub;
a plurality of support struts distributed radially around a periphery of a distal end of the hub and each support strut of the plurality of support struts extending from a proximal anchor end that is directly affixed to the hub distally in a semi-circular shape;
a plurality of anchor struts distributed radially around the periphery of the distal end of the hub, each anchor strut of the plurality of anchor struts extending distally from a first end coupled to the hub in a semi-circular arc to a distal end including an arrow-shaped anchor element and each anchor strut is separated from an adjacent anchor strut by two support struts of the plurality of support struts; and
a membrane extending distally away from the hub and covering the plurality of anchor struts and the plurality of support struts,
wherein upon deployment the plurality of support struts, the plurality of anchor struts and the membrane combine to form a semi-circular shape extending from the hub, and wherein the membrane is affixed to an outer surface of an entire length of the plurality of support struts and the plurality of anchor struts with the arrow-shaped anchor element on the distal end of each anchor strut extending through the membrane.

11. The airway valve apparatus of claim 10, wherein each anchor strut of the plurality of anchor struts includes the anchor element extending radially outward from the distal end of the anchor strut, the anchor element configured to engage a wall of the airway.

12. The airway valve apparatus according to claim 11:
wherein the plurality of support struts is configured to collapse towards a rod assembly and the anchor elements are configured to disengage the wall of the airway by engaging and pulling on a proximal end of the rod assembly.

13. The airway valve apparatus of claim 10, wherein a first anchor portion of the plurality of anchor struts has at least a first stiffness value, a first support portion of the plurality of support struts has at least a second stiffness value, and wherein the first stiffness value is greater than the second stiffness value.

14. The airway valve apparatus of claim 13:
wherein the first stiffness value is twenty percent higher than the second stiffness value.

15. The airway valve apparatus of according to claim 13:
wherein the first support portion, a second support portion of the plurality of support struts, or both are configured to partially and temporarily collapse towards a rod assembly when subjected to and during a high-pressure event on the membrane.

16. The airway valve apparatus according to claim 10:
wherein the airway valve apparatus comprises the plurality of anchor struts including three or more anchor struts and the plurality of support struts including two or more support struts disposed in-between each of the three or more anchor struts.

17. The airway valve apparatus according to claim 10:
wherein the plurality of support struts have a base width and an end width, and the base width is greater than the end width.

18. The airway valve apparatus of claim 10:
wherein a first anchor portion of the plurality of anchor struts has at least a first stiffness value, a first support portion of the plurality of support struts has at least a second stiffness value, and the first stiffness value is greater than the second stiffness value; and
wherein each support strut of the plurality of support struts has a base width in the first support portion and an end width in a second support portion, the base width being larger than the end width, and the first support portion exerting a greater radial force than the second support portion.

19. The airway valve apparatus of claim 10:
wherein a first anchor portion of the plurality of anchor struts has at least a first stiffness value, a first support portion of the plurality of support struts has at least second stiffness value, and the first stiffness value is greater than the second stiffness value; and wherein the first anchor portion exerts a greater radial force than in a second anchor portion in the plurality of anchor struts.

* * * * *